(12) United States Patent
Parrish et al.

(10) Patent No.: US 10,545,209 B2
(45) Date of Patent: *Jan. 28, 2020

(54) **SYSTEM AND METHOD FOR ACQUIRING BOTH T2\*-WEIGHTED AND T1-WEIGHTED DATA IN A SINGLE ACQUISITION USING A SINGLE DOSE OF CONTRAST AGENT**

(71) Applicants: Todd Parrish, Evanston, IL (US); Yu Fen Chen, Chicago, IL (US)

(72) Inventors: Todd Parrish, Evanston, IL (US); Yu Fen Chen, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 274 days.

This patent is subject to a terminal disclaimer.

(21) Appl. No.: 15/101,166

(22) PCT Filed: Dec. 2, 2013

(86) PCT No.: PCT/US2013/072607
§ 371 (c)(1),
(2) Date: Jun. 2, 2016

(87) PCT Pub. No.: WO2015/084301
PCT Pub. Date: Jun. 11, 2015

(65) Prior Publication Data
US 2016/0313424 A1    Oct. 27, 2016

(51) Int. Cl.
*G01V 3/00*         (2006.01)
*G01R 33/50*        (2006.01)
(Continued)

(52) U.S. Cl.
CPC ........... *G01R 33/50* (2013.01); *G01R 33/482* (2013.01); *G01R 33/483* (2013.01);
(Continued)

(58) Field of Classification Search
CPC ............ G01R 33/4816; G01R 33/4818; G01R 33/482; G01R 33/4822; G01R 33/4824;
(Continued)

(56) References Cited

U.S. PATENT DOCUMENTS 5,685,305 A    11/1997   Moonen et al.
6,754,521 B2    6/2004   Prince
(Continued)

FOREIGN PATENT DOCUMENTS

WO    2008147921 A1    12/2008

OTHER PUBLICATIONS

Sladky, et al., Slice-Timing Effects and Their Correction in Functional MRI, NeuroImage, 2011, 58:588-594.
(Continued)

*Primary Examiner* — Raul J Rios Russo
(74) *Attorney, Agent, or Firm* — Quarles & Brady LLP; Jonathan Stone

(57) ABSTRACT

Described here are systems and methods for obtaining measurements of both tissue perfusion and permeability with a magnetic resonance imaging ("MRI") system after the administration of a single dose of contrast agent. To this end, the MRI system is directed to acquire T2\*-weighted data, during which the acquired signal values are monitored for a trigger event. When the trigger event occurs, the MRI system is directed to switch from acquiring the T2\*-weighted data to acquiring T1-weighted data. The systems and methods of the present invention can thus be used for a fully automated, single acquisition of perfusion and permeability measurements using only a single dose of contrast agent.

22 Claims, 3 Drawing Sheets

(51) Int. Cl.
*G01R 33/48* (2006.01)
*G01R 33/483* (2006.01)
*G01R 33/56* (2006.01)
*G01R 33/563* (2006.01)
*G01R 33/54* (2006.01)
*G01R 33/567* (2006.01)
*A61B 5/055* (2006.01)

(52) U.S. Cl.
CPC ..... *G01R 33/4816* (2013.01); *G01R 33/4818* (2013.01); *G01R 33/4822* (2013.01); *G01R 33/4824* (2013.01); *G01R 33/4826* (2013.01); *G01R 33/4828* (2013.01); *G01R 33/4831* (2013.01); *G01R 33/4833* (2013.01); *G01R 33/4835* (2013.01); *G01R 33/4836* (2013.01); *G01R 33/4838* (2013.01); *G01R 33/5601* (2013.01); *G01R 33/56366* (2013.01); *A61B 5/055* (2013.01); *G01R 33/543* (2013.01); *G01R 33/5602* (2013.01); *G01R 33/5676* (2013.01)

(58) Field of Classification Search
CPC ............ G01R 33/4826; G01R 33/4828; G01R 33/483; G01R 33/4831; G01R 33/4833
USPC .................................................. 324/300–322
See application file for complete search history.

(56) References Cited

U.S. PATENT DOCUMENTS

| | | | |
|---|---|---|---|
| 6,804,546 | B1 | 10/2004 | Thompson et al. |
| 7,639,010 | B2 | 12/2009 | Park |
| 7,705,597 | B2 | 4/2010 | Horger et al. |
| 2003/0028101 | A1* | 2/2003 | Weisskoff .............. A61B 5/055 600/431 |
| 2004/0044281 | A1* | 3/2004 | Jesberger ............. A61B 5/0261 600/419 |
| 2004/0210130 | A1* | 10/2004 | Prince .................... A61B 5/411 600/420 |
| 2007/0264200 | A1* | 11/2007 | Small ..................... A61B 5/055 424/9.36 |
| 2008/0119720 | A1* | 5/2008 | Carroll ................. A61B 5/0263 600/410 |
| 2009/0264733 | A1* | 10/2009 | Corum ................... A61B 5/055 600/420 |
| 2013/0123611 | A1* | 5/2013 | Riederer ............ G01R 33/4818 600/419 |
| 2016/0270687 | A1* | 9/2016 | Brady-Kalnay ....... A61B 5/055 |
| 2018/0038933 | A1* | 2/2018 | Parrish .................. G01R 33/50 |

OTHER PUBLICATIONS

PCT International Search Report and Written Opinion, PCT/US2013/0072607, dated Apr. 15, 2014.

* cited by examiner

SYSTEM AND METHOD FOR ACQUIRING BOTH T2*-WEIGHTED AND T1-WEIGHTED DATA IN A SINGLE ACQUISITION USING A SINGLE DOSE OF CONTRAST AGENT

CROSS-REFERENCE TO RELATED APPLICATIONS

This application represents the US National Stage of International Patent application PCT/US2013/72607 filed Dec. 2, 2013, which is incorporated herein by reference for all purposes.

BACKGROUND OF THE INVENTION

The field of the invention is systems and methods for magnetic resonance imaging ("MRI"). More particularly, the invention relates to systems and methods for obtaining both perfusion and permeability measurements in a single data acquisition using a single administration of contrast agent.

Obtaining perfusion and permeability measures in brain tissue is critical for diagnosis and treatment planning. Perfusion-weighted data can be acquired with an MRI system using a T2*-weighted or T2-weighted pulse sequence during the first pass of a contrast agent. These exams typically run for 90-180 seconds depending on the protocol. From the perfusion-weighted data, perfusion measurements, such as blood volume in the tissue, blood flow in the tissue, and mean transit time can be computed.

Recent developments have indicated that it is possible to monitor the leakage of contrast from the blood plasma to a tumor or lesion. This leakage is monitored by dynamic T1-weighted imaging and requires scanning for 4-8 minutes post administration of the contrast agent. Furthermore, some pre-contrast imaging is required to provide information for the models that generate the permeability measures.

Currently, perfusion and permeability studies are conducted on different days to allow the use of full does of contrast. This is expensive because it requires two sessions. It is also inconvenient for the patient, who must make two separate trips for the different imaging scans.

As an alternative approach, perfusion and permeability studies can be conducted serially using two separate administrations of levels of contrast agent to minimize the patient's exposure to the contrast agent. These measurements are thus compromised by the non-optimal levels of contrast agent.

In light of the foregoing, it would be desirable to provide a system and method capable of obtaining both perfusion and permeability measurements in a single imaging session using an MRI system and a single, full dose of contrast agent.

SUMMARY OF THE INVENTION

The present invention overcomes the aforementioned drawbacks by providing a method for directing a magnetic resonance imaging ("MRI") system to acquire both T2*-weighted data and T1-weighted data from a subject in which a single dose of contrast agent is present. The method includes administering a dose of a contrast agent to the subject, or imaging a subject to which a dose of contrast agent has already been administered. The MRI system is directed to acquire T2*-weighted data from the subject while the dose of contrast agent is present in the subject, for example during the first pass of the contrast agent. Signal values in the T2*-weighted data are monitored for a trigger event while the MRI system is acquiring the T2*-weighted data. The MRI system is then directed to acquire T1-weighted data from the subject while the dose of contrast agent is present in the subject by switching from a T2*-weighted pulse sequence to a T1-weighted pulse sequence when the trigger event occurs.

The trigger event may include monitoring the signal values for a peak negative signal value and then monitoring the signal values for a recovery to a stable signal value, which may be the baseline value, whereby when the recovery to the stable signal value occurs the MRI system switches from the T2*-weighted pulse sequence to the T1-weighted pulse sequence.

The trigger event may also include monitoring the signal values for a peak negative signal value, then monitoring the signal values for a recovery to a percent of a baseline signal value, and then waiting a delay time after the recovery to the percent of the baseline is detected, whereby the MRI system switches from the T2*-weighted pulse sequence to the T1-weighted pulse sequence after the delay time. The delay time may be in a range of about 3-9 seconds.

The trigger event may also include monitoring the signal values for a peak negative signal value and then waiting a delay time after the peak negative value is detected, whereby the MRI system switches from the T2*-weighted pulse sequence to the T1-weighted pulse sequence after the delay time. The time it takes the signal values to decrease from baseline to the peak negative value can be measured, and the delay time can be set as twice this time. The delay time may also be in a range of about 7-15 seconds.

The trigger event may also include monitoring the signal values for a percent decrease from a baseline signal value and then waiting a delay time after the percent decrease from the baseline signal value is detected, whereby the MRI system switches from the T2*-weighted pulse sequence to the T1-weighted pulse sequence after the delay time. The delay time may be in a range of about 12-25 seconds.

Monitoring the signal values for the trigger event may include monitoring signal values in a selected region-of-interest ("ROI"). The ROI can be a slice location within an image volume from which the T2*-weighted data is acquired. The ROI can also be a subset of a slice location within an image volume from which the T2*-weighted data is acquired. The ROI can also be a subvolume of an image volume from which the T2*-weighted data is acquired. The ROI can also be the entire image volume from which the T2*-weighted data is acquired. The ROI can also be located outside of an image volume from which the T2*-weighted data is acquired and the monitoring step can include acquiring additional T2*-weighted data from the region-of-interest.

It is another aspect of the invention to compute perfusion parameters from the T2*-weighted data.

It is still another aspect of the invention to provide baseline T1-weighted data acquired from the subject and to compute tissue permeability measurements from the baseline T1-weighted data and the acquired T1-weighted data. Providing the baseline T1-weighted data may include acquiring the baseline T1-weighted data before the contrast agent is administered to the subject.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full

DETAILED DESCRIPTION OF THE INVENTION

Described here are systems and methods for obtaining measurements of both tissue perfusion and permeability with a magnetic resonance imaging ("MRI") system after the administration of a single dose of contrast agent. To this end, the systems and methods described here include the acquisition of a first data type, such as perfusion-weighted data, during which the acquired magnetic resonance signals are monitored for a trigger event. When the trigger event occurs, the MRI system is directed to switch from acquiring the first data type to a second data type, such as T1-weighted image data. The systems and methods of the present invention can advantageously be used for a fully automated, single acquisition of perfusion and permeability measurements using only a single dose of contrast agent.

The systems and methods described here thus allow the automatic collection of both perfusion-weighted data and data from which permeability measurements can be computed using only a single full dose of contrast. The imaging setup includes the placement of region-of-interest ("ROI") in, or outside of, the target anatomy. Placement of the ROI can be done manually or automatically. This ROI is monitored for the trigger event that will switch the MRI system between the two data acquisition schemes. The resulting data can be processed with standard perfusion software to compute perfusion measurements, and can also be processed to calculate permeability measures.

In some embodiments, the ROI can be positioned within the target anatomy for which the perfusion and permeability measurements are desired. As an example, the ROI can be a single slice location in the target anatomy or a subset of that slice location. As another example, the ROI can be a volume-of-interest that covers the whole target anatomy or a subset thereof. For instance, the target anatomy can be the brain and the ROI can be positioned within a location in the brain.

In some embodiments, the ROI can be positioned outside of the target anatomy for which the perfusion and permeability measurements are desired. As an example, the ROI can be a single slice location outside of the target anatomy, or a subset of that slice location outside of the target anatomy. For instance, the target anatomy can be the brain and the ROI can a slice location, or subset thereof, that covers the carotid artery.

Figure 1:
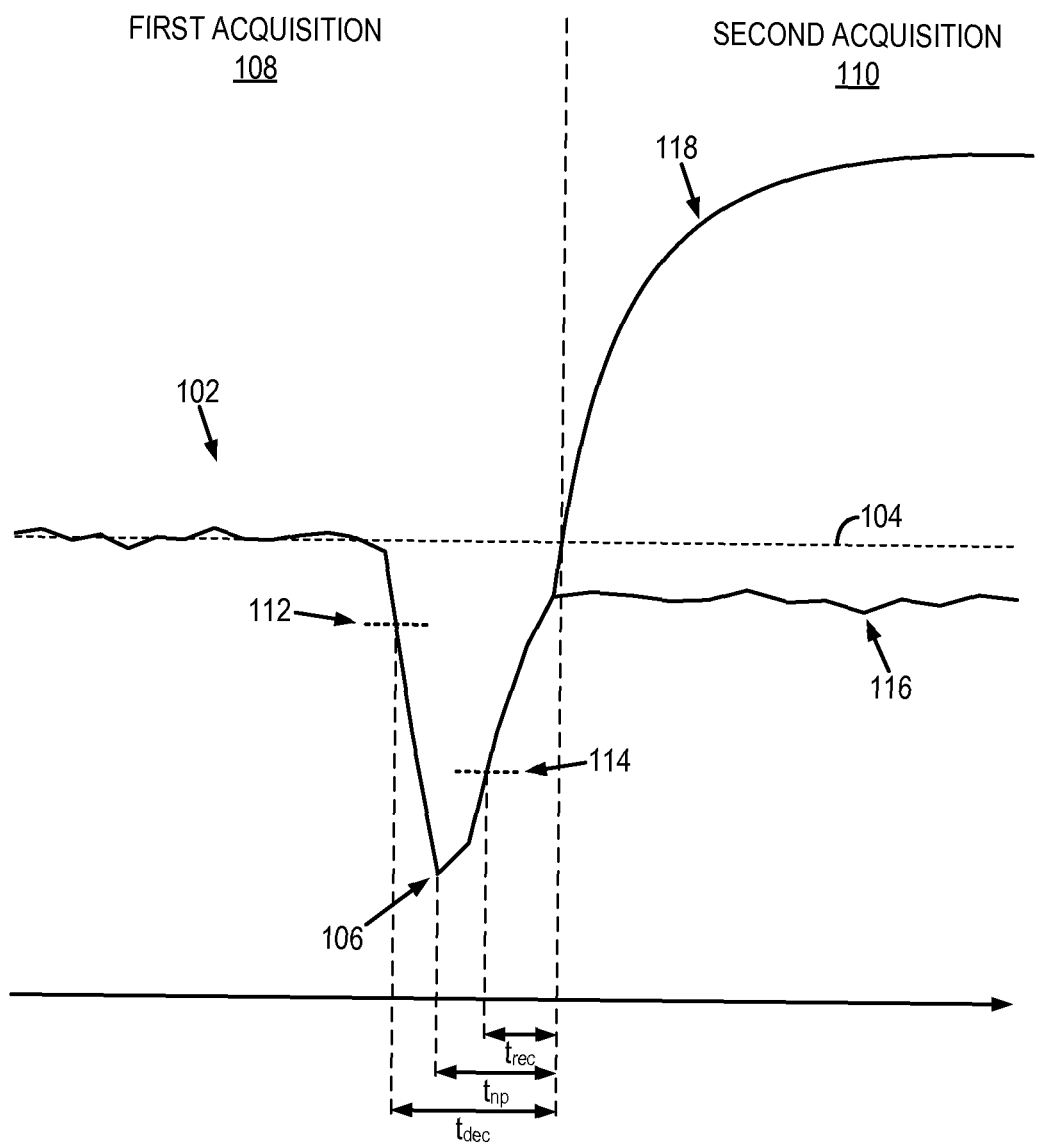
FIG. 1 illustrates an example of a magnetic resonance signal intensity curve following the administration of a contrast agent to a subject.

Referring now to FIG. 1, an example of the signal intensity evolution following the administration of a single dose of contrast agent is illustrated. In this example, the signal 102 starts around a baseline level 104. After a period of time, the signal 102 begins to decrease towards a peak negative value 106, after which the signal 102 generally recovers back to a stable signal level 116, which may or may not be the baseline signal value 104. In general, the signal 102 plateaus and fluctuates around the stable signal value 116 as a result of recirculation of the contrast agent. In some instances, the stable signal value 116 may be the same as the baseline signal value 104. In some regions, however, significant T1-enhancement will occur, resulting in a T1-enhanced signal 118 in those regions. As will be described below with several non-limiting examples, the trigger event that switches the MRI system between data acquisition schemes is based on monitoring this signal 102.

In some embodiments, the trigger can be measuring a return to a stable signal level 116 after the peak negative value 106 occurs. For instance, the MRI system can monitor for the occurrence of the peak negative value 106. When this value occurs, the MRI system switches to monitoring for a recovery to the stable signal value 116. When recovery to the stable value 116 is reached, the MRI system will transition from the first acquisition 108 to the second acquisition 110. In some instances, the trigger can be made if the signal goes above the baseline value 104 following the peak signal loss, which indicates a high level of leakage. Preferably, recovery to the stable signal value 116 is monitored in a larger region-of-interest, such as a whole slice or a whole volume. Using a larger region-of-interest for monitoring diminishes the potential for local T1-enhancement signals 118 to obfuscate the stable signal value 116.

The trigger event just mentioned is preferable because it is not dependent on selecting a delay time that may be different based on the particular subject. For instance, if the subject is a stroke patient, the time delays might be longer due to the lack of blood flow. If the subject is a tumor patient, however, the time delays might be shorter because the blood flow may be normal or increased, especially in higher grade tumors.

In some embodiments, the trigger can be a preset time delay, $t_{np}$, from the detection of the peak negative signal 106. For instance the time delay, $t_{np}$, can be twice the time it takes the signal to change from baseline 104 to that peak negative value 106. As an example, if it takes 10 seconds for the signal to change from baseline 104 to the peak negative value 106, the time delay, $t_{np}$, would be set as 20 seconds starting from the occurrence of the peak negative signal 106. Using this parameter as the trigger can provide for rapid image reconstruction, making it robust for general clinical MRI systems. The delay time, $t_{np}$, can also be set as a delay time on the order of 7.5-10 seconds in tumor patients and 10-15 seconds for stroke patients.

In some embodiments, the trigger can be a preset time delay, $t_{dec}$, from the detection of a specific relative decrease from the baseline signal value 104. For instance, the MRI system can monitor for a certain percentage decrease 112 in signal from the baseline signal value 104. As an example, the percentage decrease can be 30 percent. In this instance, the time delay, $t_{dec}$, may be on the order of 12-15 seconds in tumor patients and 20-25 seconds for stroke patients.

In some embodiments, the trigger can be a preset time delay, $t_{rec}$, from the detection of a specific relative recovery from the peak negative signal value 106. For instance, the MRI system can monitor for a certain percentage of signal recovery 114 to baseline 104 from the peak negative value 106. As an example, the MRI system may monitor for the occurrence of the peak negative signal value 106. After the peak negative signal value 106 occurs, the MRI system may then monitor for a certain percentage of recovery 114 back to baseline 104. As an example, the percentage of recovery can be 50 percent. In this instance, the time delay, $t_{rec}$, may be on the order of 3-4.5 seconds in tumor patients and 7-9 seconds for stroke patients. As the trigger point moves closer to a complete recovery to baseline 104, the predictability of the delay time, $t_{rec}$, increases. As a trade-off, however, as the trigger point moves closer to the end of the signal recovery curve the likelihood of missing potential data to be acquired increases. This drawback is not too severe, however, since the likelihood of missing a significant amount of potential data to acquire is low.

Figure 2:
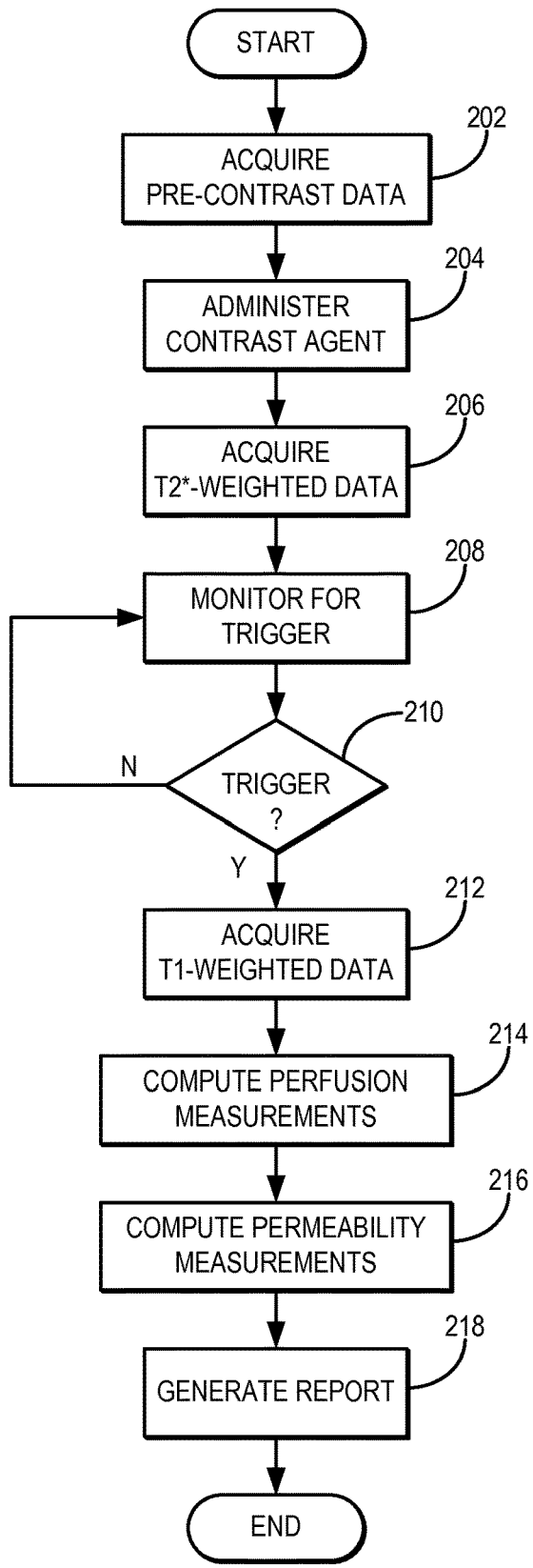
FIG. 2 is a flowchart setting forth the steps of an example of a method that is capable of acquiring both T2*-weighted and T1-weighted data in a single acquisition using a single dose of contrast agent.

Referring now to FIG. 2, a flowchart setting forth the steps of an example of a method for acquiring both perfusion data and permeability data with an MRI system and using a single dose of contrast agent is illustrated. The method begins with providing baseline data acquired from the subject without contrast, as indicated at step 202. For instance, the baseline data can be acquired from the subject with the MRI system prior to the subsequent imaging steps. As an example, the baseline data can be obtained using a T1-weighted imaging sequence, such as a spoiled gradient ("SPGR") pulse sequence, and may be a two-dimensional or, preferably, a three-dimensional acquisition.

The method proceeds with the administration of a contrast agent to the subject, as indicated at step 204. Preferably, only a single dose of contrast agent is administered to the subject. This is in contrast to other methods, where a separate dose of contrast agent is administered for each different imaging sequence. While the contrast agent is present in the subject, perfusion-weighted data is acquired, as indicated at step 206. Any suitable imaging pulse sequence can be used to obtain this perfusion-weighted data. For instance, perfusion-weighted data can be acquired with a T2*-weighted or T2-weighted pulse sequence during the first pass of the contrast agent. These exams typically run for 90-180 seconds depending on the protocol. As an example, perfusion-weighted data can be acquired using a spin-echo echo-planar imaging ("EPI") pulse sequence or a gradient-echo EPI pulse sequence.

As it is being acquired, the perfusion-weighted data is monitored for a trigger event that will direct the MRI system to switch from the perfusion-weighted data acquisition to the T1-weighted data acquisition, as indicated at step 208. Examples of monitoring for a trigger event are described above. When the trigger event occurs, the MRI system switches to acquiring T1-weighted data, as determined at decision block 210. T1-weighted data is then acquired while the same single dose of contrast agent is still present in the subject, as indicated at step 212. Any suitable imaging pulse sequence can be used to obtain this T1-weighted data. For instance, an SPGR sequence can be used to acquire two-dimensional or, preferably, three-dimensional T1-weighted data.

From the perfusion-weighted data, perfusion parameters are computed, as indicated at step 214. These computations can be performed using techniques known in the art. For instance, images can be reconstructed from the perfusion-weighted data and these images can be processed to compute measurements of blood volume, blood flow, and mean transit time. From the baseline data and the T1-weighted data acquired while the contrast agent was present in the subject, permeability parameters are computed, as indicated at step 216. These computations can be performed using techniques known in the art. For instance, images can be reconstructed from both the baseline and later-acquired T1-weighted data, from which measurements of tissue permeability can be computed.

The method can include generating a report of the measured perfusion and permeability of the target tissue, as indicated at step 218. For instance, the generated report can include displaying perfusion maps, permeability maps, or both to a clinician. As another example, the generated report can include presenting one or more a numerical values associated with a perfusion or permeability measurement. As still another example, the generated report can include presenting information to a clinician that is determined on the basis of the perfusion and permeability measurements. For instance, the generated report may indicate a particular tissue or disease state. As another example, the generated report can indicate a tumor response to a particular treatment, or can be used to grade a tumor. As still another example, the generated report can be used to asses the severity of a stroke or the risk for future hemorrhage.

Figure 3:
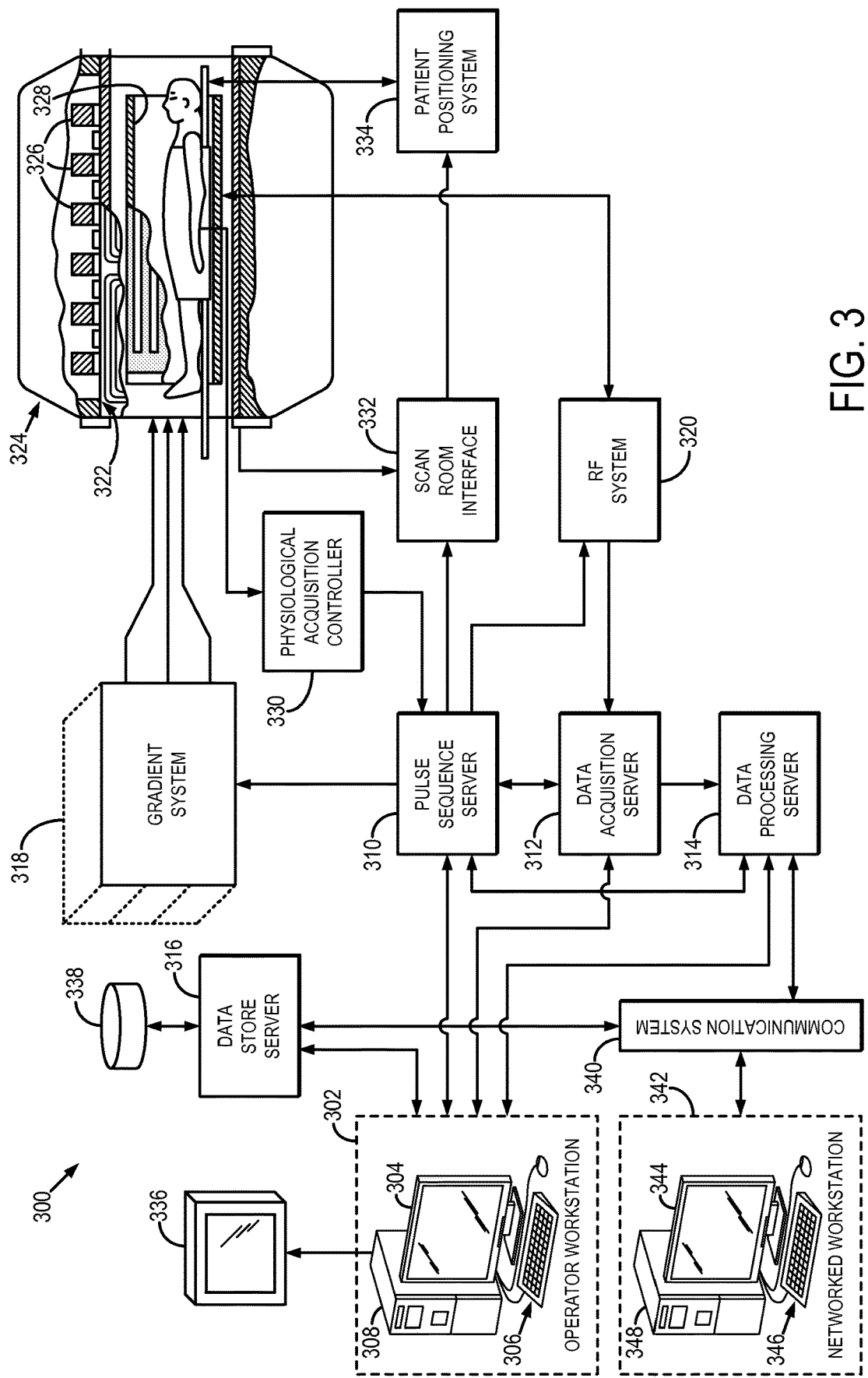
FIG. 3 is a block diagram of an example of a magnetic resonance imaging ("MRI") system.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, the data acquisition server 312 can be programmed to monitor for one or more of the trigger events described above and to direct the pulse sequence server 310 to switch from a first pulse sequence used to acquire a first data type, such as T2*-weighted data, to a second pulse sequence used to acquire a second data type, such as T1-weighted data.

In another example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for directing a magnetic resonance imaging (MRI) system to acquire T2*-weighted data and T1-weighted data from a subject in which a single dose of contrast agent is present, the steps comprising:
    a) administering a dose of a contrast agent to the subject;
    b) acquiring with the MRI system, T2*-weighted data from the subject while the dose of contrast agent is present in the subject using a T2*-weighted pulse sequence;
    c) monitoring with the MRI system, signal values in the T2*-weighted data for a trigger event while the MRI system is acquiring the T2*-weighted data; and d) when the trigger event occurs, acquiring with the MRI system T1-weighted data from the subject while the dose of contrast agent is present in the subject using a T1-weighted pulse sequence, wherein the MRI system automatically switches from the T2*-weighted pulse sequence to the T1-weighted pulse sequence when the trigger event occurs.

2. The method as recited in claim 1, wherein the trigger event comprises monitoring the signal values for a peak negative signal value and then monitoring the signal values for a recovery to a stable signal value, whereby when the recovery to the stable signal occurs the MRI system switches from the T2*-weighted pulse sequence to the T1-weighted pulse sequence.

3. The method as recited in claim 1, wherein the trigger event comprises monitoring the signal values for a peak negative signal value, then monitoring the signal values for a recovery to a percent of a baseline signal value, and then waiting a delay time after the recovery to the percent of the baseline is detected, whereby the MRI system switches from the T2*-weighted pulse sequence to the T1-weighted pulse sequence after the delay time.

4. The method as recited in claim 3, wherein the delay time is in a range of about 3 to 9 seconds.

5. The method as recited in claim 1, wherein the trigger event comprises monitoring the signal values for a peak negative signal value and then waiting a delay time after the peak negative value is detected, whereby the MRI system switches from the T2*-weighted pulse sequence to the T1-weighted pulse sequence after the delay time.

6. The method as recited in claim 5, wherein step c) includes measuring a time during which the signal values decrease from a baseline signal value to the peak negative value and setting the delay time as twice the time taken for the signal values decrease from the baseline signal value to the peak negative value.

7. The method as recited in claim 5, wherein the delay time is in a range of about 7 to 15 seconds.

8. The method as recited in claim 1, wherein the trigger event comprises monitoring the signal values for a percent decrease from a baseline signal value and then waiting a delay time after the percent decrease from the baseline signal value is detected, whereby the MRI system switches from the T2*-weighted pulse sequence to the T1-weighted pulse sequence after the delay time.

9. The method as recited in claim 8, wherein the delay time is in a range of about 12 to 25 seconds.

10. The method as recited in claim 1, wherein monitoring the signal values in step c) comprises monitoring signal values in a selected region-of-interest.

11. The method as recited in claim 10, wherein the region-of-interest is a slice location within an image volume from which the T2*-weighted data is acquired.

12. The method as recited in claim 10, wherein the region-of-interest is a subset of a slice location within an image volume from which the T2*-weighted data is acquired.

13. The method as recited in claim 10, wherein the region-of-interest is a subvolume of an image volume from which the T2*-weighted data is acquired.

14. The method as recited in claim 10, wherein the region-of-interest is an entire image volume from which the T2*-weighted data is acquired.

15. The method as recited in claim 10, wherein the region-of-interest is located outside of an image volume from which the T2*-weighted data is acquired and step c) comprises acquiring additional T2*-weighted data from the region-of-interest.

16. The method as recited in claim 1, further comprising computing perfusion parameters from the T2*-weighted data acquired in step b).

17. The method as recited in claim 1, further comprising providing baseline T1-weighted data acquired from the subject and computing tissue permeability measurements from the baseline T1-weighted data and the T1-weighted data acquired in step d).

18. The method as recited in claim 17, further comprising computing perfusion parameters from the T2*-weighted data acquired in step b).

19. The method as recited in claim 18, further comprising generating a report using the computed perfusion parameters and the computed tissue permeability measurements.

20. The method as recited in claim 19, wherein the generated report includes at least one of an image indicating the computed perfusion parameters and an image indicating the computed tissue permeability measurements.

21. The method as recited in claim 3, wherein the percent of the baseline signal value to which the signal values recover is 50 percent.

22. The method as recited in claim 8, wherein the percent decrease from the baseline signal value is 30 percent.

* * * * *